(12) United States Patent
Treiser (10) Patent No.: US 12,222,517 B2
(45) Date of Patent: Feb. 11, 2025

(54) LASER SYSTEM DELIVERING ULTRA-SHORT PULSES ALONG MULTIPLE BEAM DELIVERY PATHS

(71) Applicant: Matthew David Treiser, Mount Vernon, NY (US)

(72) Inventor: Matthew David Treiser, Mount Vernon, NY (US)

( * ) Notice: Subject to any disclaimer, the term of this patent is extended or adjusted under 35 U.S.C. 154(b) by 0 days.

(21) Appl. No.: 18/377,969

(22) Filed: Oct. 9, 2023

(65) Prior Publication Data

US 2024/0036337 A1 Feb. 1, 2024

Related U.S. Application Data

(63) Continuation of application No. 17/831,216, filed on Jun. 2, 2022, now Pat. No. 11,782,283, which is a
(Continued)

(51) Int. Cl.
*G02B 27/09* (2006.01)
*A61F 9/008* (2006.01)
(Continued)

(52) U.S. Cl.
CPC .............. *G02B 27/09* (2013.01); *A61F 9/008* (2013.01); *A61F 9/00804* (2013.01);
(Continued)

(58) Field of Classification Search
CPC ........... A61B 2018/20553; A61B 2018/00642; A61B 2018/20353; A61B 2018/00452; A61B 2018/00785; A61B 2018/00601; A61B 2018/00464; A61B 2018/0577; G02B 27/10; G02B 27/12; G02B 27/101; G02B 27/0025; G02B 27/0068;
(Continued)

(56) References Cited

U.S. PATENT DOCUMENTS 6,169,631 B1 1/2001 Xuan et al.
8,702,770 B2 4/2014 Hanft et al.
(Continued)

FOREIGN PATENT DOCUMENTS

| CN | 1266298 A | 9/2000 |
|---|---|---|
| EP | 1470623 B1 | 9/2006 |
| WO | WO2013156421 A1 | 10/2013 |
| WO | WO2020/055723 A1 | 3/2020 |

*Primary Examiner* — Sultan Chowdhury
(74) *Attorney, Agent, or Firm* — The Belles Group, P.C.

(57) ABSTRACT

A laser system includes a laser source generating a laser beam having ultra-short pulses; a laser delivery assembly optically receiving the laser beam and comprising: a beam splitter configured to split the laser beam between a first beam delivery path and a second beam delivery path; and at least one focusing lens optically coupled to the beam splitter and configured to focus the laser beam from each of the first beam delivery path and the second beam delivery path to a focal point on a predefined plane; wherein the first beam delivery path intersects the predefined plane at a first angle, the second beam delivery path intersects the predefined plane at a second angle, and a first pulse from the first beam delivery path and a second pulse from the second beam delivery path are coincident at the focal point.

20 Claims, 4 Drawing Sheets

Related U.S. Application Data continuation of application No. 16/564,307, filed on Sep. 9, 2019, now Pat. No. 11,353,714.

(60) Provisional application No. 62/728,927, filed on Sep. 10, 2018.

(51) Int. Cl.
    *G02B 27/00*     (2006.01)
    *G02B 27/10*     (2006.01)

(52) U.S. Cl.
    CPC ......... *G02B 27/0025* (2013.01); *G02B 27/10* (2013.01); *A61F 9/0084* (2013.01)

(58) Field of Classification Search
    CPC ............ G02B 27/0875; G02B 27/1093; A61F 9/008; A61F 9/0084; A61F 9/00804; A61F 9/00812; A61F 9/00814; A61F 9/00825; A61F 9/00863; A61F 9/00889; A61F 9/00895
See application file for complete search history.

(56) References Cited

U.S. PATENT DOCUMENTS

| | | |
|---|---|---|
| 10,092,771 B2 | 10/2018 | Varghese et al. |
| 11,353,714 B2 | 6/2022 | Treiser |
| 2007/0258119 A1 | 11/2007 | Munday et al. |
| 2008/0151238 A1 | 6/2008 | Zhu et al. |
| 2009/0149843 A1 | 6/2009 | Smits et al. |
| 2010/0324543 A1 | 12/2010 | Kurtz et al. |
| 2011/0028957 A1* | 2/2011 | Raksi ................... A61F 9/00825 606/6 |
| 2011/0118713 A1 | 5/2011 | Raksi et al. |
| 2011/0305256 A1 | 12/2011 | Chann et al. |
| 2012/0253333 A1 | 10/2012 | Garden et al. |
| 2014/0276672 A1 | 9/2014 | Lee et al. |
| 2015/0290030 A1 | 10/2015 | Suckewer et al. |
| 2015/0362714 A1* | 12/2015 | Iga ....................... G02B 21/002 359/372 |
| 2016/0045367 A1 | 2/2016 | Horvath et al. |
| 2016/0120700 A1 | 5/2016 | Han et al. |
| 2018/0259760 A1* | 9/2018 | Condello ............. G02B 21/002 |
| 2019/0135678 A1* | 5/2019 | Liu .................... B23K 26/0617 |
| 2020/0345236 A1 | 11/2020 | Beckman et al. |

\* cited by examiner

LASER SYSTEM DELIVERING ULTRA-SHORT PULSES ALONG MULTIPLE BEAM DELIVERY PATHS

CROSS-REFERENCE TO RELATED APPLICATIONS

This application is a continuation of U.S. patent application Ser. No. 17/831,216, filed on Jun. 2, 2022, that is a continuation of U.S. patent application Ser. No. 16/564,307, filed on Sep. 9, 2019, and issued as U.S. Pat. No. 11,353,714 on Jun. 7, 2022, that claims the benefit of U.S. Provisional Patent Application No. 62/728,927, filed on Sep. 10, 2018, the entire disclosures of all of which are incorporated herein by reference, for all purposes.

BACKGROUND OF THE INVENTION

Lasers which generate ultra-short pulses have found numerous applications across a wide variety of industries, including both industrial manufacturing applications to medical applications, among others. Current technologies utilize ablative lasers (e.g., CO2 or Er:YAG) to provide localized destruction of substrate materials. In the medical field, these substrate materials are generally soft tissues, and ablation of the tissues is used to promote skin remodeling and healing. This technique has been shown to be beneficial in skin rejuvenation, aesthetic improvement of the skin, treatment of hypertrophic scars, removal of unwanted pigments and/or skin lesions, to assist in drug delivery, and for oncological treatment. One potential drawback of these laser treatments is that they often result in destruction of all layers of the skin until the desired treatment depth is achieved. This results in epidermal destruction and an inability to target specific layers of the skin and underlying tissues without injury to the more superficial layers.

Multiphoton technologies utilize non-linear photonic absorption to excite molecules, particularly for microscopy purposes. Utilizing the multiphoton concept, a target is excited utilizing two or more photons, each having a lower energy (and subsequently longer wavelengths) than standard energies needed to cause non-linear excitement. Energies from the multiple photons are concentrated at the focal point of the lens such that the probability of this non-linear excitement is extremely low except at the focal point. Utilizing a high flux of photons provided by a laser that generates ultra-short pulses and near-infrared to infrared emissions, such as a femtosecond laser, the density of photons may be increased at the desired focal depth while also reducing the probability of damaging surface layers of the tissue and other subsurface layers that reside above the targeted layer. Therefore, excitation occurs primarily at the desired depth with little scatter and good penetration depth secondary to the use of longer wavelengths (i.e., near infra-red.). While these technologies have been utilized for imaging of 3D tissues, there has been limited clinical application of these technologies for the treatment of the skin and deeper tissues. Part of the reason for this is that such treatments require increased energy, which in turn increases the probability of tissue damage to the layers of tissue above that layer being treated.

SUMMARY OF THE INVENTION

Exemplary embodiments according to the present disclosure are directed to a laser system which generates ultra-short pulses to make sub-surface modifications in a targeted layer of a substrate while also substantially reducing the probability that layers of substrate above the targeted layer will not be damaged during the process. In the medical field, the substrate may be skin, subcutaneous tissues, fat, and blood vessels, among other types of tissues. Specifically, the laser system may include tuneable optics which enable greater control of ablative energies only to targeted subsurface tissues and not to overlying or underlying tissues. This allows for treatment of individual layers of tissue without damage to adjacent tissues.

In one separate aspect, the invention may be a laser system including: a laser source generating a laser beam including ultra-short pulses; a laser delivery assembly optically coupled to the laser source to receive the laser beam, the laser delivery assembly including: a beam splitter configured to split the laser beam between a first beam delivery path and a second beam delivery path; and at least one focusing lens optically coupled to the beam splitter and configured to focus the laser beam from each of the first beam delivery path and the second beam delivery path to a focal point on a predefined plane; wherein the first beam delivery path intersects the predefined plane at a first angle, the second beam delivery path intersects the predefined plane at a second angle, and a first pulse from the first beam delivery path and a second pulse from the second beam delivery path are coincident at the focal point.

In another aspect, the invention may be a method of modifying a substrate, the method including: generating a laser beam including ultra-short pulses; splitting the laser beam between a first beam delivery path and a second beam delivery path; focusing the laser beam from each of the first beam delivery path and the second beam delivery path to a focal point on a predefined plane within the substrate, the first beam delivery path intersecting the predefined plane at a first angle, and the second beam delivery path intersecting the predefined plane at a second angle; and wherein a first pulse from the first beam delivery path and a second pulse from the second beam delivery path are coincident at the focal point.

In still another aspect, the invention may be a laser system including: a laser source generating a laser beam including femtosecond pulses; a laser delivery assembly optically coupled to the laser source to receive the laser beam, the laser delivery assembly including: a beam splitter configured to split the laser beam between a first beam delivery path and a second beam delivery path; a first focusing lens optically coupled to the beam splitter and positioned within the first beam delivery path, the first focusing lens configured to focus the laser beam from the first beam delivery path to a focal point on a predefined plane; a second focusing lens optically coupled to the beam splitter and positioned within the second beam delivery path, the second focusing lens configured to focus the laser beam from the second beam delivery path to the focal point on the predefined plane; wherein the first beam delivery path intersects the predefined plane at a first angle, the second beam delivery path intersects the predefined plane at a second angle, and a first pulse from the first beam delivery path and a second pulse from the second beam delivery path are coincident at the focal point.

In yet another aspect, the invention may be a method of modifying a substrate, the method including: generating a laser beam including femtosecond pulses; splitting the laser beam between a first beam delivery path and a second beam delivery path; focusing the laser beam from the first beam delivery path to a focal point on a predefined plane within a substrate using a first focusing lens disposed in the first beam delivery path, the first beam delivery path intersecting the predefined plane at a first angle; focusing the laser beam from the second beam delivery path to the focal point on the predefined plane using a second focusing lens disposed in the second beam delivery path, the second beam delivery path intersecting the predefined plane at a second angle; and wherein a first pulse from the first beam delivery path and a second pulse from the second beam delivery path are coincident at the focal point.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION OF THE INVENTION

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention is not be limited to such preferred embodiments illustrating some possible non-limiting combinations of features that may exist alone or in other combinations of features; the scope of the invention therefore should not be limited unless otherwise expressly stated in the claims appended hereto.

In the context of the embodiments described herein, optics and optical systems are disclosed which include one or more optical elements. It is to be understood that various ones of the optical elements could be replaced by a plurality of other optical elements which provide the same functionality. Further, other optical elements could be included as part of the optical systems described herein in order to provide additional functionality beyond that which is expressly disclosed or described herein. The scope of the claims are not to be limited unless otherwise expressly stated therein.

Figure 1:
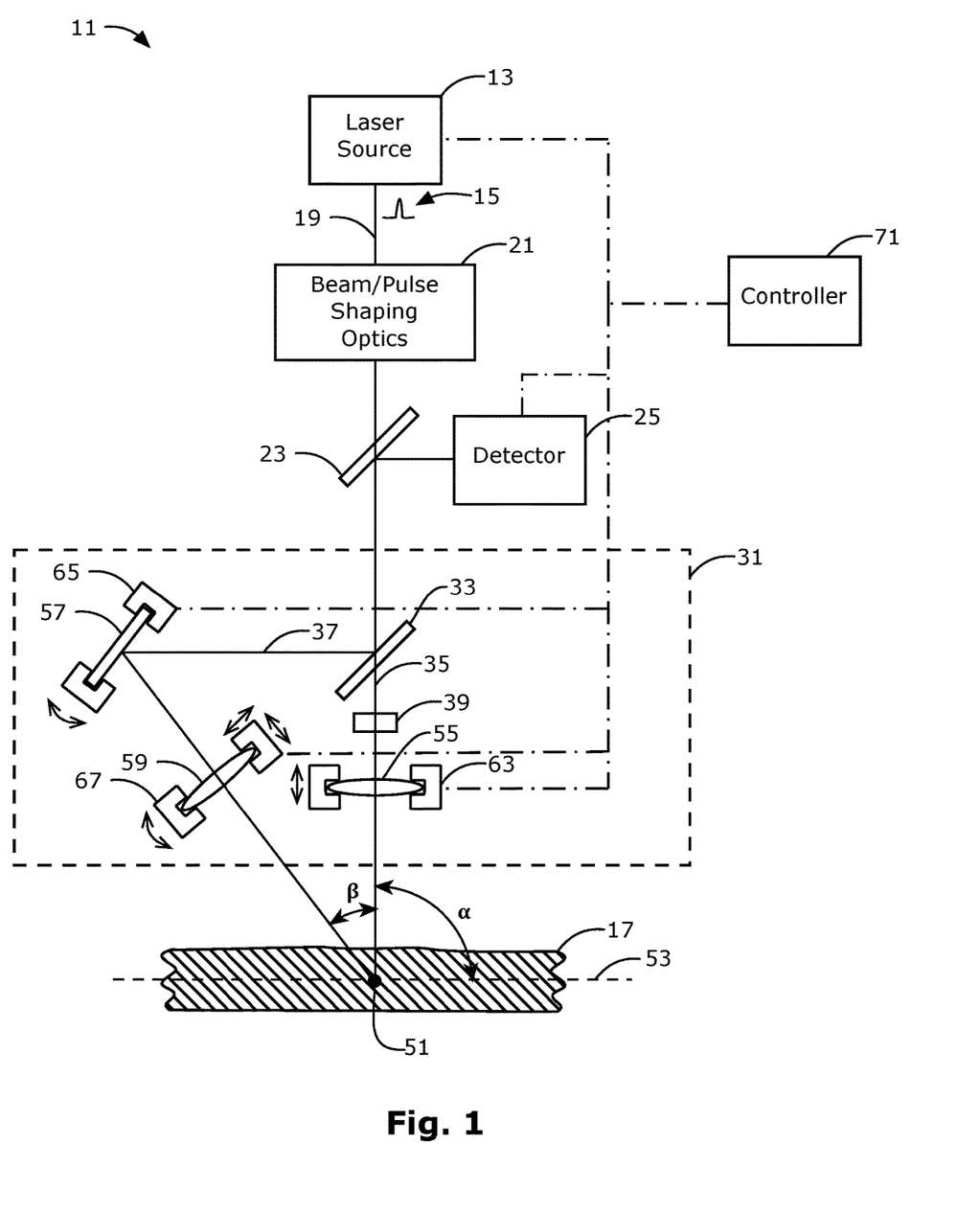
FIG. 1 is schematic illustration of a first embodiment of a laser system which delivers ultra-short pulses along multiple beam delivery paths.

Turning in detail to the drawings, FIG. 1 illustrates a laser system 11 which includes a laser source 13 configured to generate a laser beam. The laser beam is formed by a plurality of ultra-short pulses 15 and is directed by a plurality of optical elements, which are discussed in detail below, toward and into a substrate 17. An ultra-short laser pulse is one that has a duration of between about 30 picoseconds and about 1 femtosecond. Advantageously, ultra-short laser pulses may be used to produce multiphoton excitation events within the substrate 17. Through such multiphoton excitation events, which are the result of interactions between the ultra-short pulses of the laser beam and the matter forming the substrate 17, the substrate 17 can be modified by the laser beam through what is known as ablation. Depending upon the substrate 17 and the intent of the operator of the laser system 11, in certain embodiments the modification may result in microstructures being formed in the substrate 17. In embodiments in which the substrate 17 is a tissue, whether the tissue is in vivo or in vitro, the modification may be elimination of a feature of the tissue, a cutting of a feature of the tissue, a separating of two features of the tissue, or any other modification that may serve a medical purpose for in vivo tissue in the determination of an attending physician or a research purpose for in vitro tissue in the determination of a researcher.

The laser beam is directed along a primary beam path 19, in which other optical elements of the laser system 11 are positioned to interact with the laser beam. In certain embodiments, the laser source 13 may be a femtosecond laser. In certain embodiments, the laser source 13 may generate the laser beam in the infrared to near-infrared wavelengths. For example, in certain embodiments the laser source 13 may be a titanium sapphire laser. In general, the longer wavelength of light in the infrared and near-infrared wavelengths results in greater tissue penetration with less scatter. In still other embodiments, the laser source 13 may generate the laser beam in any other spectrum that is appropriate to create a multiphoton excitation event within a target substrate or within a specific layer of a target substrate. In certain embodiments, the laser source 13 may be a tunable pulsed laser source. Such tunable pulsed laser sources are well known to those of ordinary skill in the art of ultra-short pulsed lasers.

From the laser source 13, the laser beam is directed along the primary beam path 19 to beam/pulse shaping optics 21, which may be used to manipulate the temporal profile of the ultra-short laser pulses. For example, the ultra-short laser pulses may undergo pulse shaping which is used to shorten or elongate the duration of the ultra-short pulses 15, or to generate complex pulse profiles. Depending upon the form of the ultra-short pulses 15 produced by the laser source 13 and the application for which the laser system 11 is being used, in certain embodiments the beam/pulse shaping optics 21 may be omitted from the laser system 11. In certain embodiments, the laser beam may pass through any number of lenses, polarizers, splitters, mirrors, and/or fibers after being generated by the laser source and before entering the substrate. Such additional optical elements, although they may be present in certain embodiments, are not to be limiting of the invention unless expressly recited in the claims.

Following the beam/pulse shaping optics 21, the laser beam is directed through a dichroic mirror 23. The dichroic mirror 23 is constructed to allow the laser beam, at the generated wavelength, to pass through unaltered. The dichroic mirror 23, does however reflect light returning in the opposite direction down the beam path, i.e., the direction starting at the substrate 17 along the beam path toward to the laser source 13, that is emitted from excitation events. Any such emitted feedback light is directed by the dichroic mirror 23 into the detector 25 so that the excitation events may be detected and analyzed as appropriate.

After passing through the dichroic mirror 23, the laser beam is directed to the laser delivery assembly 31, within which the laser beam is incident upon a beam splitter 33. The beam splitter 33 splits the primary beam path 19 into a first beam delivery path 35 and a second beam delivery path 37. The laser beam is thus also divided between the first beam delivery path 35 and the second beam delivery path 37. By dividing the laser beam between the first and second beam delivery paths 35, 37, the power of the pulses traveling along each path is less than the power of each pulse traveling along the primary beam path 19. By appropriate selection of the beam splitter 33, the power of each pulse from the primary beam path 19 can be approximately divided in half between the first and second beam delivery paths 35, 37.

As shown, the beam splitter 33 uses reflection to split the laser beam between the first and second beam delivery paths 35, 37. In certain embodiments, the beam splitter 33 may instead use refraction to split the laser beam between the first and second beam delivery paths 35, 37. One such example of a refractive beam splitter is a grating. Other types of reflective and/or refractive beam splitters may also be used.

From the point that the laser beam is separated by the beam splitter 33 to the focal point 51 within the substrate 17, the power of each pulse traveling along each of the first and second beam delivery paths 35, 37 is reduced such that the ultra-short pulses with reduced energy do not have sufficient power to cause a multiphoton excitation event within the substrate 17. Instead, a multiphoton excitation event may only be caused when the energies from pulses propagating along each of the first and second beam delivery paths 35, 37 are recombined when coincident at the focal point 51 within the substrate 17.

In order to achieve the desired coincidence at the focal point 51, the optical path length of the first and second beam delivery paths 35, 37, between the point of incidence of the primary beam path 19 with the beam splitter 33 and the focal point 51, should be the same. As shown in FIG. 1, the first beam delivery path 35 is has an optical path length that is shorter than the optical path length of the second beam delivery path 37. To compensate for this difference in optical path lengths, a time delay optical element 39 is placed within the first beam delivery path 35. This time delay optical element 39 serves to slow down pulses traveling along the first beam delivery path 35 so that the effective optical path length of the first beam delivery path 35 is the same as the optical path length of the second beam delivery path 37. In certain embodiments, the time delay optical element 39 is a plate of glass having an index of refraction that is greater than the index of refraction of atmosphere, to slow down the pulses in the first beam delivery path 35, and a thickness that is sufficient to introduce the desired delay. In certain embodiments, the beam splitter 33 can also perform the function of providing the desired time delay by selection of a beam splitter with a width sufficient to introduce the desired delay.

A first focusing lens 55 is in the first beam delivery path 35 and positioned to focus the laser beam from the first beam delivery path 35 to the focal point 51. The focal point 51 lies within a predefined plane 53 that extends through the substrate 17. In FIG. 1, the laser beam from the first beam delivery path 35 is normal to the predefined plane 53, such that the angle α between the laser beam from the first beam delivery path 35 and the predefined plane 53 is fixed at 90°. Thus, for the laser beam from the first beam delivery path 35 of this embodiment, the predefined plane 53 is also the focal plane of the first focusing lens 55.

A mirror 57 and a second focusing lens 59 are in the second beam delivery path 37. The mirror 57 is optically positioned to direct the laser beam reflected from the beam splitter 33 along the second beam delivery path 37 to the second focusing lens 59, and the second focusing lens 59 is positioned to focus the laser beam from the second beam delivery path 37 to the focal point 51, such that the laser beam from both the first and second beam delivery paths 35, 37 are coincident at the focal point 51. In FIG. 1, the laser beam from the second beam delivery path 37 is at an acute angle β with respect to the predefined plane 53. Thus, in this embodiment, the angle β between the laser beam from the second beam delivery path 37 with respect to the predefined plane 53 is less than the angle α between the laser beam from the first beam delivery path 35 and the predefined plane 53.

The laser system 11 includes a positioning assembly, which for simplicity in FIG. 1 is depicted by the support structures 63, 65, 67. Although not shown explicitly, it should be understood that the positioning assembly, including the support structures 63, 65, 67, also includes one or more servo motors or other rotary/linear actuators, electronics, and other components which enable the positioning assembly to move the various optical components as shown and described. Such mechanical positioning assemblies are well known to those of skill in the art of rotary and linear actuator systems. The positioning assembly, through the support structures 63, 65, 67, is configured to move the first and second focusing lenses 55, 59 and the mirror 57. In certain embodiments, the mirror 57 and the support structure 65 may be a single unit in the form of a steering mirror. In certain of these embodiments, a fast steering mirror may be used for the mirror 57 and the support structure 65.

The laser system 11 also includes a controller 71 which is operably coupled to the laser source 13, the detector 25, and each of the support structures 63, 65, 67 through control lines to enable full control of the laser system 11, including positioning of the focal point 51 and operation of the laser source 13 so that the substrate 17 can be modified. The controller 71 enables simultaneous control over each of the support structures 63, 65, 67 to ensure that the laser beam from both the first and second beam delivery paths 35, 37 coincide at the focal point 51. In certain embodiments, the controller 71 may be pre-programmed to perform a desired modification to the substrate 17 so that the modification process can be automated. In certain other embodiments, the controller 71 may be operated by a user to enable control of the modification process in real time.

The support structure 63 supports the first focusing lens 55 and enables translation of the first focusing lens 55 toward and away from the substrate. Translation of the first focusing lens 55 toward the substrate moves the focal point 51, and also the predefined plane 53, deeper into the substrate 17. Similarly, translation of the first focusing lens 55 away from the substrate moves the focal point 51, and thus also the predefined plane 53, toward the surface of the substrate 17.

The support structure 65 supports the mirror 57 and enables rotation of the mirror 57 about a central point of the reflective surface of the mirror 57. The support structure 67 supports the second focusing lens 59 and enables translation of the second focusing lens 59 in two directions, the first direction being toward and away from the substrate along an optical axis of the second focusing lens 59, and the second direction being orthogonal to the first direction. The support structure 67 also enables rotation of the second focusing lens 59 about one or more axes orthogonal to the optical axis of the second focusing lens 59. In combination, by being able to rotate the mirror 57 and independently rotate and translate the second focusing lens 59, the laser beam from the second beam delivery path 37 may be brought to focus at the focal point 51, so that the laser beam from each of the first and second beam delivery paths 35, 37 coincide at the focal point 51.

In certain embodiments, the laser delivery assembly 61 and the support structures 63, 65, 67 may be incorporated into a handheld device. In such an embodiment, the controller 71 may control the depth of the focal point 51 within the substrate, while the user manually controls lateral movement of the focal point 51 within the predefined plane 53. Alternatively, in such an embodiment the user may operate the controller to set the focal point 51 at a fixed distance from the support structure 63, thereby requiring the user to manually control the depth of the focal point 51 within the substrate 17 while also manually controlling lateral movement of the focal point 51 within the predefined plane 53.

In the embodiment shown, the beam delivery paths 35, 37 are shown as having different optical path lengths. In certain embodiments, a refractive beam splitter may be employed, instead of the reflective beam splitter shown, in lieu of introducing a time delay into one of the beam delivery paths. In certain other embodiments, additional optical elements may be introduced into the shorter of the two paths so that the beam delivery paths 35, 37 have the same optical path length.

In certain embodiments of the laser delivery assembly 31, additional beam delivery paths may be added by placement of the appropriate optical components. Any such additional beam delivery paths that are introduced into the laser delivery assembly 31 may use any of the beam steering and beam focusing techniques expressly or impliedly disclosed herein. Such additional delivery paths may have the same or different optical path lengths as compared to the beam delivery paths 35, 37.

Figure 2:
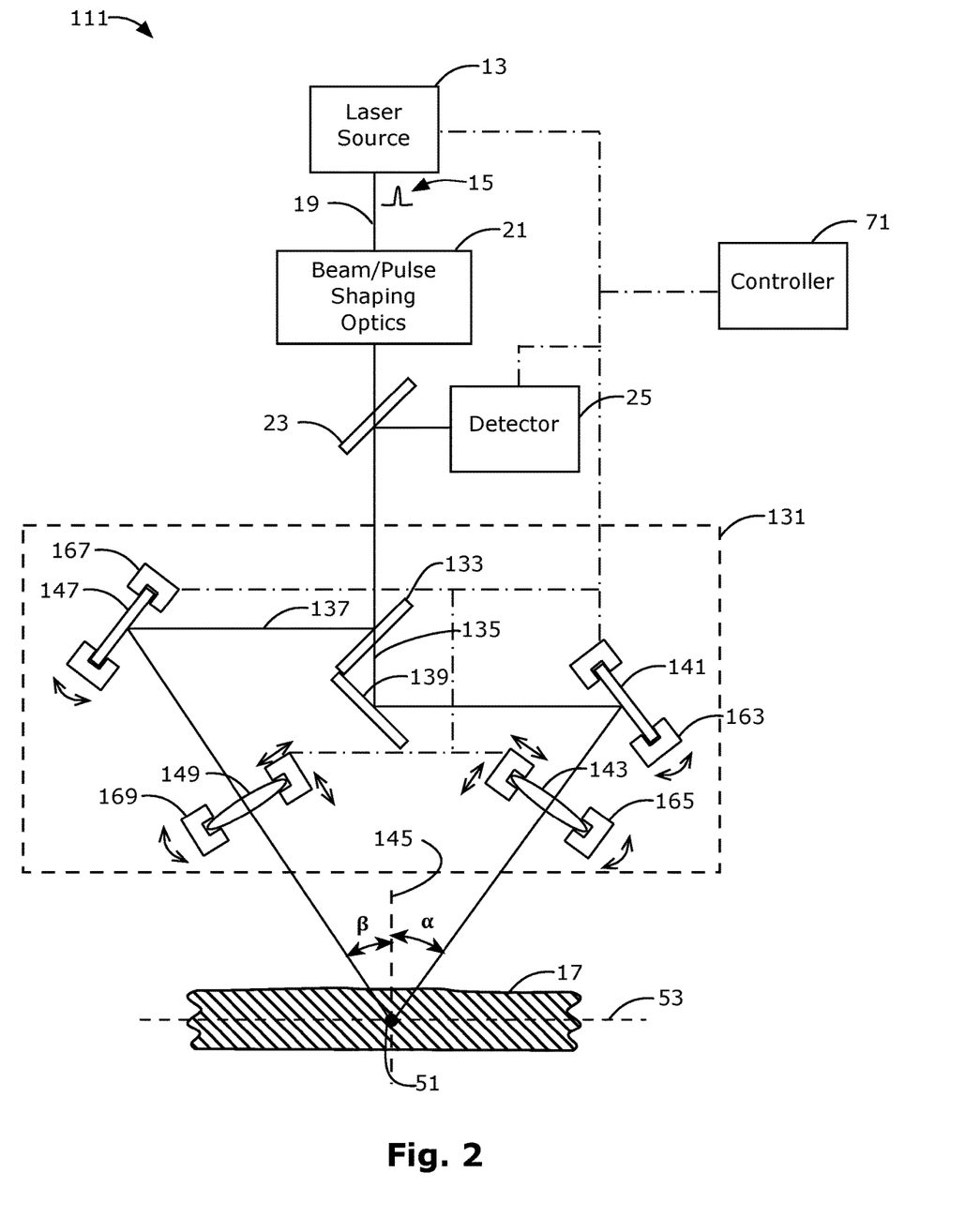
FIG. 2 is schematic illustration of a second embodiment of a laser system which delivers ultra-short pulses along multiple beam delivery paths.

FIG. 2 illustrates another embodiment of a laser system 111 which may be used to modify a substrate 17. The laser system 111 includes a laser source 13 configured to generate a laser beam formed by a plurality of ultra-short pulses 15, and the laser beam is directed toward and into the substrate 17. In certain embodiments, the laser source 13 may be a femtosecond laser. In certain embodiments, the laser source 13 may generate the laser beam in the infrared to near-infrared wavelengths. In certain embodiments, the laser source 13 may be a tunable pulsed laser source.

The laser beam is directed along a primary beam path 19, in which other optical elements of the laser system 111 are positioned to interact with the laser beam. From the laser source 13, the laser beam is directed along the primary beam path 19 to beam/pulse shaping optics 21, which may be used to manipulate the temporal profile of the ultra-short laser pulses. Again, depending upon the form of the ultra-short pulses 15 produced by the laser source 13 and the application for which the laser system 111 is being used, in certain embodiments the beam/pulse shaping optics 21 may be omitted from the laser system 111. In certain embodiments, the laser beam may pass through any number of lenses, polarizers, splitters, mirrors, and/or fibers after being generated by the laser source and before entering the substrate. Such additional optical elements, although they may be present in certain embodiments, are not to be limiting of the invention unless expressly recited in the claims.

Following the beam/pulse shaping optics 21, the laser beam is directed through a dichroic mirror 23, which allows the laser beam to pass through and directs light emitted from excitation events into the detector for feedback and analysis.

After passing through the dichroic mirror 23, the laser beam is directed to the laser delivery assembly 131, within which the laser beam is incident upon the beam splitter 133. The beam splitter 133 splits the primary beam path 19 into a first beam delivery path 135 and a second beam delivery path 137. The laser beam is thus also divided between the first beam delivery path 135 and the second beam delivery path 137, in the same manner as previously described.

As shown, the beam splitter 133 uses reflection to split the laser beam between the first and second beam delivery paths 135, 137. In certain embodiments, other types of reflective and/or refractive beam splitters may also be used.

In order to achieve the desired coincidence at the focal point 51, the optical path length of the first and second beam delivery paths 135, 137, between the point of incidence of the primary beam path 19 with the beam splitter 133 and the focal point 51, should be the same. As discussed above, a time delay optical element may be incorporated into the laser delivery assembly 131 as needed.

A first mirror 139 is in the first beam delivery path 135 immediately following the beam splitter 133. This first mirror 139 is in a fixed position and directs the laser beam along the first beam delivery path 135 to a second mirror 141, which in turn directs the laser beam along the first beam delivery path 135 to a first focusing lens 143. The first focusing lens 143 is positioned to focus the laser beam from the first beam delivery path 135 to the focal point 51. In FIG. 2, the laser beam from the first beam delivery path 135 is at an acute angle α with respect to the normal 145 of the predefined plane 53.

A third mirror 147 and a second focusing lens 149 are in the second beam delivery path 137. The third mirror 147 is optically positioned to direct the laser beam reflected from the beam splitter 133 along the second beam delivery path 137 to the second focusing lens 149, and the second focusing lens 149 is positioned to focus the laser beam from the second beam delivery path 137 to the focal point 51, such that the laser beam from both the first and second beam delivery paths 135, 137 are coincident at the focal point 51. In FIG. 2, the laser beam from the second beam delivery path 137 is at an acute angle β with respect to the normal 145 of the predefined plane 53. In this embodiment, due the symmetry of the positions of the first and second focusing lenses 143, 149, the angle β and the angle α are equivalent.

The laser system 111 includes a positioning assembly, which for simplicity in FIG. 2 is depicted by the support structures 163, 165, 167, 169. Although not shown explicitly, it should be understood that the positioning assembly, including the support structures 163, 165, 167, 169, also includes one or more servo motors or other rotary/linear actuators, electronics, and other components which enable the positioning assembly to move the various optical components as shown and described. The positioning assembly, through the support structures 163, 165, 167, 169, is configured to move the first and second focusing lenses 143, 149 and the second and third mirrors 141, 147. In certain embodiments, each of the second and third mirrors 141, 147 and the respective support structures 163, 167 may be a single unit in the form of a steering mirror or a fast steering mirror.

The laser system 111 also includes a controller 71 which is operably coupled to the laser source 13, the detector 25, and each of the support structures 163, 165, 167, 169 through control lines to enable full control of the laser system 111, including positioning of the focal point 51 and operation of the laser source 13 so that the substrate 17 can be modified. The controller 71 enables simultaneous control over each of the support structures 163, 165, 167, 169 to ensure that the laser beam from both the first and second beam delivery paths 135, 137 coincide at the focal point 51. In certain embodiments, the controller 71 may be pre-programmed to perform a desired modification to the substrate 17 so that the modification process can be automated. In certain other embodiments, the controller 71 may be operated by a user to enable control of the modification process in real time.

The support structure 163 supports the second mirror 141 and enables rotation of the second mirror 141 about a central point of the reflective surface of the second mirror 141. The support structure 165 supports the first focusing lens 143 and enables translation of the first focusing lens 143 in two directions, the first direction being toward and away from the substrate along an optical axis of the first focusing lens 143, and the second direction being orthogonal to the first direction. The support structure 165 also enables rotation of the first focusing lens 143 about one or more axes orthogonal to the optical axis of the first focusing lens 143. In combination, by being able to rotate the second mirror 141 and independently rotate and translate the first focusing lens 143, the laser beam from the first beam delivery path 137 may be brought to focus at the focal point 51. This combination of movement also enables the focal point 51, and also the predefined plane 53, to be moved deeper into the substrate 17 or toward the surface of the substrate 17.

The support structure 167 supports the third mirror 147 and enables rotation of the third mirror 147 about a central point of the reflective surface of the third mirror 147. The support structure 169 supports the second focusing lens 149 and enables translation of the second focusing lens 149 in two directions, the first direction being toward and away from the substrate along an optical axis of the second focusing lens 149, and the second direction being orthogonal to the first direction. The support structure 169 also enables rotation of the second focusing lens 149 about one or more axes orthogonal to the optical axis of the second focusing lens 149. In combination, by being able to rotate the third mirror 147 and independently rotate and translate the second focusing lens 149, the laser beam from the second beam delivery path 137 may be brought to focus at the focal point 151, so that the laser beam from each of the first and second beam delivery paths 135, 137 coincide at the focal point 51.

In certain embodiments, the laser delivery assembly 131 and the support structures 163, 165, 167, 169 may be incorporated into a handheld device. In such an embodiment, the controller 71 may control the depth of the focal point 51 within the substrate, while the user manually controls lateral movement of the focal point 51 within the predefined plane 53. Alternatively, in such an embodiment the user may operate the controller to set the focal point 51 at a fixed distance from the laser delivery assembly 131, thereby requiring the user to manually control the depth of the focal point 51 within the substrate 17 while also manually controlling lateral movement of the focal point 51 within the predefined plane 53.

In the embodiment shown, the beam delivery paths 135, 137 are shown as having different optical path lengths. In certain embodiments, a refractive beam splitter may be employed, instead of the reflective beam splitter shown, in lieu of introducing a time delay into one of the beam delivery paths. In certain other embodiments, additional optical elements may be introduced into the shorter of the two paths so that the beam delivery paths 135, 137 have the same optical path length.

In certain embodiments of the laser delivery assembly 131, additional beam delivery paths may be added by placement of the appropriate optical components. Any such additional beam delivery paths that are introduced into the laser delivery assembly 131 may use any of the beam steering and beam focusing techniques expressly or impliedly disclosed herein. Such additional delivery paths may have the same or different optical path lengths as compared to the beam delivery paths 135, 137.

Figure 3:
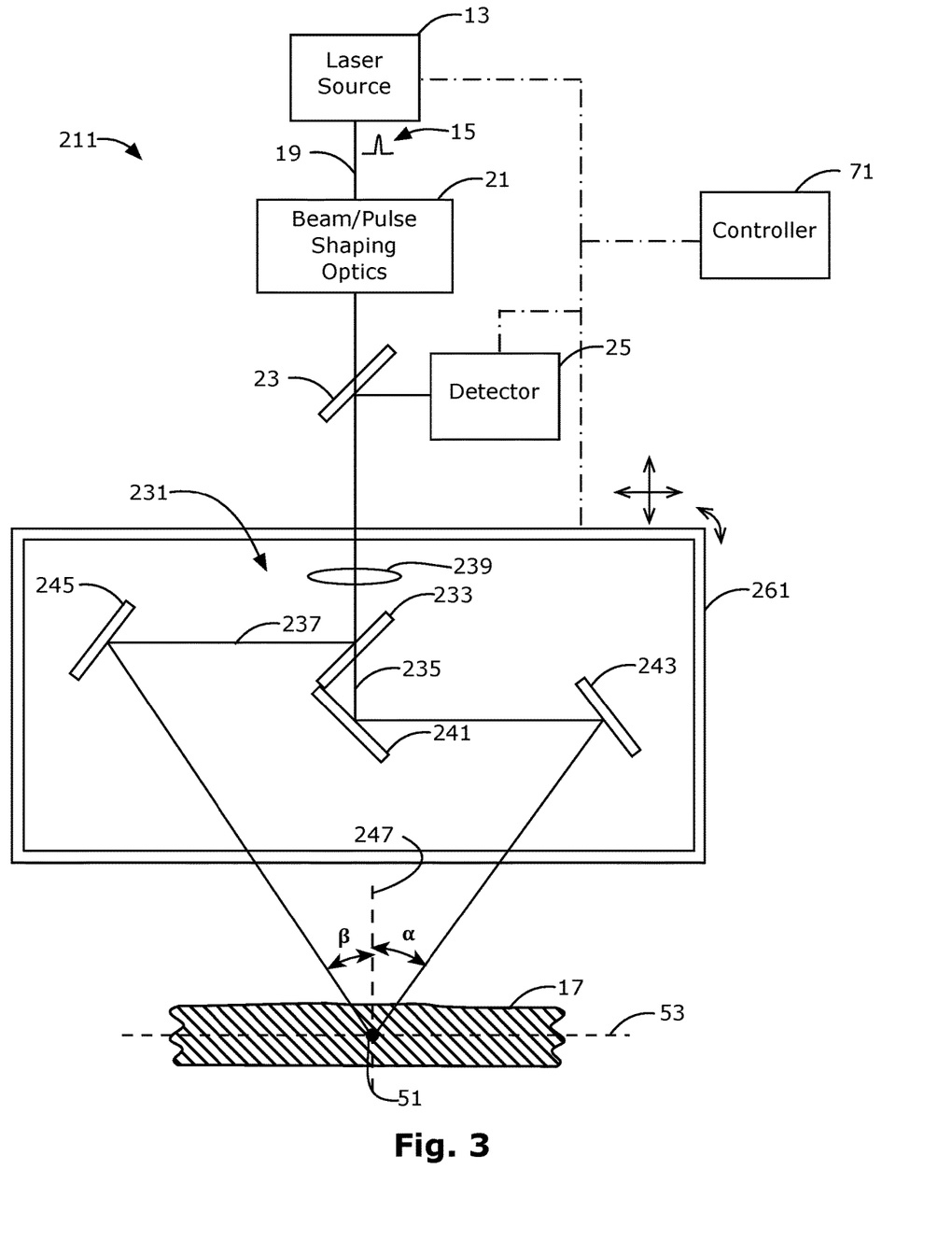
FIG. 3 is schematic illustration of a third embodiment of a laser system which delivers ultra-short pulses along multiple beam delivery paths.

FIG. 3 illustrates another embodiment of a laser system 211 which may be used to modify a substrate 17. The laser system 211 includes a laser source 13 configured to generate a laser beam formed by a plurality of ultra-short pulses 15, and the laser beam is directed toward and into the substrate 17. In certain embodiments, the laser source 13 may be a femtosecond laser. In certain embodiments, the laser source 13 may generate the laser beam in the infrared to near-infrared wavelengths. In certain embodiments, the laser source 13 may be a tunable pulsed laser source.

The laser beam is directed along a primary beam path 19, in which other optical elements of the laser system 211 are positioned to interact with the laser beam. From the laser source 13, the laser beam is directed along the primary beam path 19 to beam/pulse shaping optics 21, which may be used to manipulate the temporal profile of the ultra-short laser pulses. Again, depending upon the form of the ultra-short pulses 15 produced by the laser source 13 and the application for which the laser system 211 is being used, in certain embodiments the beam/pulse shaping optics 21 may be omitted from the laser system 211. In certain embodiments, the laser beam may pass through any number of lenses, polarizers, splitters, mirrors, and/or fibers after being generated by the laser source and before entering the substrate. Such additional optical elements, although they may be present in certain embodiments, are not to be limiting of the invention unless expressly recited in the claims.

Following the beam/pulse shaping optics 21, the laser beam is directed through a dichroic mirror 23, which allows the laser beam to pass through and directs light emitted from excitation events into the detector for feedback and analysis.

After passing through the dichroic mirror 23, the laser beam is directed to the laser delivery assembly 231, which is housed within the positioning assembly 261. Within the laser delivery assembly 231, the laser beam passes through a focusing mirror 239, after which the beam splitter 233 splits the primary beam path 19 into a first beam delivery path 235 and a second beam delivery path 237. The laser beam is thus also divided between the first beam delivery path 235 and the second beam delivery path 237, in the same manner as previously described. The focusing mirror 239 focuses the laser beam passing along both the first and second beam delivery paths 237, 237 at the focal point 51.

As shown, the beam splitter 233 uses reflection to split the laser beam between the first and second beam delivery paths 235, 237. In certain embodiments, other types of reflective and/or refractive beam splitters may also be used.

In order to achieve the desired coincidence at the focal point 51, the optical path length of the first and second beam delivery paths 235, 237, between the point of incidence of the primary beam path 19 with the beam splitter 233 and the focal point 51, should be the same. As discussed above, a time delay optical element may be incorporated into the laser delivery assembly 231 as needed.

A first mirror 241 is in the first beam delivery path 235 immediately following the beam splitter 233. This first mirror 239 is in a fixed position and directs the laser beam along the first beam delivery path 235 to a second mirror 243, which is also in a fixed position. The second mirror 243 in turn directs the laser beam along the first beam delivery path 235 to the focal point 51. In FIG. 3, the laser beam from the first beam delivery path 235 is at an acute angle $\alpha$ with respect to the normal 247 of the predefined plane 53.

A third mirror 245 is in the second beam delivery path 237. The third mirror 245 is in a fixed position in order to direct the laser beam reflected from the beam splitter 233 along the second beam delivery path 237 to the focal point 51, such that the laser beam from both the first and second beam delivery paths 235, 237 are coincident at the focal point 51. In FIG. 3, the laser beam from the second beam delivery path 237 is at an acute angle $\beta$ with respect to the normal 145 of the predefined plane 53. In this embodiment, due the symmetry of the positions of the first and second mirrors 243, 245, the angle $\beta$ and the angle $\alpha$ are equivalent.

The positioning assembly 261, which for simplicity in FIG. 2 is depicted by an enclosure, should be understood to also include one or more servo motors or other rotary/linear actuators, electronics, and other components which enable the positioning assembly to move the laser delivery assembly 231 as shown and described.

The laser system 211 also includes a controller 71 which is operably coupled to the laser source 13, the detector 25, and the positioning assembly 261 through control lines to enable full control of the laser system 211, including positioning of the laser delivery assembly 231 and operation of the laser source 13 so that the substrate 17 can be modified. In certain embodiments, the controller 71 may be preprogrammed to perform a desired modification to the substrate 17 so that the modification process can be automated. In certain other embodiments, the controller 71 may be operated by a user to enable control of the modification process in real time.

In certain embodiments, positioning assembly 261 may be incorporated into a handheld device. In such an embodiment, the controller 71 may control the depth of the focal point 51 within the substrate, while the user manually controls lateral movement of the focal point 51 within the predefined plane 53. Alternatively, in such an embodiment the user may operate the controller to set the focal point 51 at a fixed distance from the laser delivery assembly 231, thereby requiring the user to manually control the depth of the focal point 51 within the substrate 17 while also manually controlling lateral movement of the focal point 51 within the predefined plane 53.

In the embodiment shown, the beam delivery paths 35, 37 are shown as having different optical path lengths. In certain embodiments, a refractive beam splitter may be employed, instead of the reflective beam splitter shown, in lieu of introducing a time delay into one of the beam delivery paths. In certain other embodiments, additional optical elements may be introduced into the shorter of the two paths so that the beam delivery paths 235, 237 have the same optical path lengths.

In certain embodiments of the laser delivery assembly 231, additional beam delivery paths may be added by placement of the appropriate optical components. Any such additional beam delivery paths that are introduced into the laser delivery assembly 231 may use any of the beam steering and beam focusing techniques expressly or impliedly disclosed herein. Such additional delivery paths may have the same or different path lengths as compared to the beam delivery paths 235, 237.

Each of the laser system embodiments described in connection with FIGS. 1-3 allow for the delivery of electromagnetic radiation energy in only at the focal point where the laser beam from the multiple beam delivery paths coincide. Moreover, the adjustability of the focal point within the substrate introduces significant versatility to the laser systems and benefits for their use. In the field of medicine, particularly for the treatment of tissue using the laser systems disclosed herein, benefits may be had over existing technologies, including one or more of: (1) lower individual energies may be used along each beam delivery path so that less adjacent tissue damage occurs; (2) the depth may be controlled more accurately as the dispersion of energies is even lower than current technology so that the probability of multiphoton non-linear excitement in an unwanted location within tissue is so low that it largely only occurs precisely at the focal point, which is the point of coincidence for the laser beam emerging from each of the multiple beam delivery paths; (3) the addition of more lenses can provide finer control of energy delivery, thus allowing both coarse and fine adjustments; (4) the increased precision allows for the ability to isolate individual layers of the tissue, such as in skin, for treatment; (5) tissues at greater depths may be treated allowing for treatment of not just skin, but also subcutaneous tissues, fat, and blood vessels.

Figure 4:
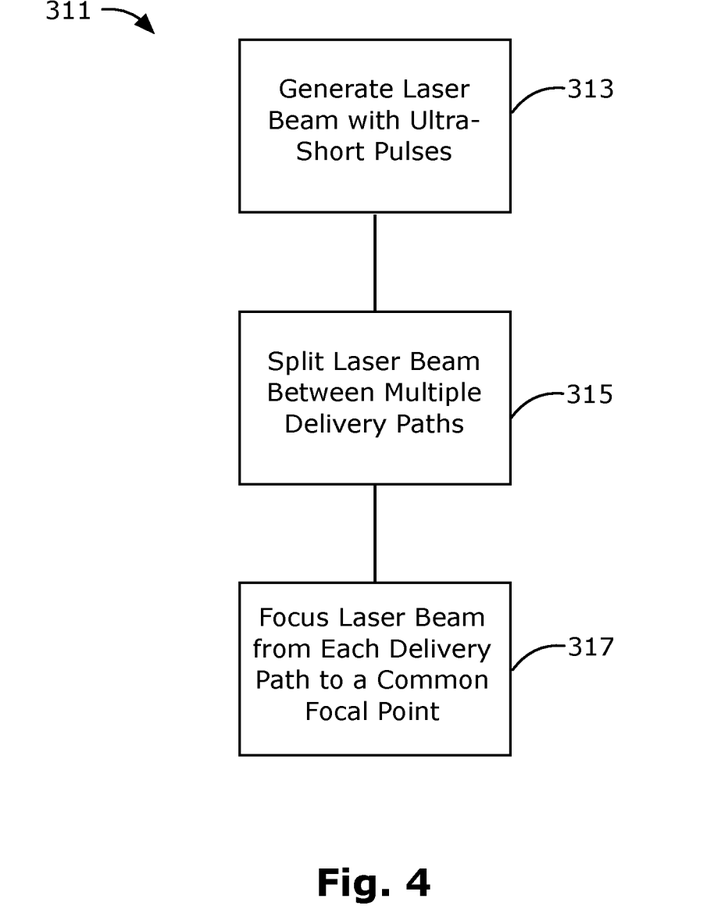
FIG. 4 is a flowchart illustrating operation of a laser system which delivers ultra-short pulses along multiple beam delivery paths.

A flowchart 311 showing a process for delivering a laser beam having ultra-short pulses along multiple mean delivery paths is shown in FIG. 4. The process of this flowchart 311 may be utilized with any of the laser system embodiments disclosed herein. Alternatively, the process of this flowchart 311 may be utilized with any other appropriate laser system which is capable of performing the process steps as set forth in the claims. Thus, the process steps are not to be limited to use with any particular laser system embodiment unless otherwise expressly recited in the claims. In the first step of the process, a laser beam having ultra-short pulses is generated 313. In certain embodiments, the laser beam may be generated by a femtosecond laser. In certain other embodiments, any laser or laser system capable of generating a series of ultra-short pulses may be used. In the following step, the generated laser beam is split 315 between multiple beam delivery paths. The number of beam delivery paths may vary. The number of beam delivery paths may be as few as two, or it may be any greater number of beam delivery paths, limited only by the resources of the process user. In certain embodiments, it may be desirable to evenly distribute the pulse energy of the laser beam amongst the multiple beam delivery paths. In certain other embodiments, the pulse energy of the laser beam may be unevenly distributed amongst the multiple delivery paths, with one or more of the beam delivery paths receiving a greater amount of pulse energy than the other beam delivery paths. In most embodiments, the distribution pulse energy is largely determined by the choice and specifications of the beam splitter. In the next step, the laser beam from each delivery path is focused 317 to a common focal point. By focusing the laser beam from each delivery path to a common focal point, the pulse energy that was previously distributed between the multiple delivery paths is made to be coincident at the focal point, so that the now recombined pulse energy may induce a multiphoton excitation event, while the laser beam from each individual beam delivery path does not include enough pulse energy to induce a multiphoton excitation event. In certain embodiments, the focusing step 317 may be performed before the splitting step 315, with the result being that the pulse energy from each delivery path is still made to be coincident at a common focal point.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A laser system comprising:
a laser source generating a laser beam comprising ultra-short pulses;
a laser delivery assembly optically coupled to the laser source to receive the laser beam, the laser delivery assembly comprising:
a beam splitter configured to split the laser beam between a first beam delivery path and a second beam delivery path;
a first focusing lens optically coupled to the beam splitter and positioned within the first beam delivery path, the first focusing lens configured to focus the laser beam from the first beam delivery path to a focal point on a predefined plane; and
a second focusing lens optically coupled to the beam splitter and positioned within the second beam delivery path, the second focusing lens configured to focus the laser beam from the second beam delivery path to the focal point on the predefined plane, the second focusing lens being further configured for focus independently relative to the focus of the first focusing lens,
wherein the first beam delivery path intersects the predefined plane at a first angle, the second beam delivery path intersects the predefined plane at a second angle, and a first pulse from the first beam delivery path and a second pulse from the second beam delivery path are coincident at the focal point, and
wherein the second focusing lens focuses light relative to the focus of the first focusing lens independently to provide an avoidance of laser energy excitation by the first pulse and the second pulse in at least one of: above the focal point, or above the predefined plane.

2. The laser system of claim 1, wherein the second angle is different from the first angle.

3. The laser system of claim 1, wherein the second angle is equivalent to the first angle.

4. The laser system of claim 1, wherein the first beam delivery path and the second beam delivery path have different path lengths.

5. The laser system of claim 1, wherein at least one of: the first focusing lens, or the second focusing lens, is in a path of the laser beam before the beam splitter.

6. The laser system of claim 1, wherein the beam splitter is in a path of the laser beam before at least one of: the first focusing lens, or the second focusing lens.

7. The laser system claim 1, further comprising a positioning assembly, the laser delivery assembly coupled to the positioning assembly, wherein the positioning assembly is configured to move at least one of: the laser delivery assembly, the first focusing lens, or the second focusing lens.

8. The laser system of claim 7, wherein the positioning assembly is configured to move the laser delivery assembly using at least one of: translation, or rotation.

9. The laser system of claim 7, wherein the positioning assembly is configured to move at least one of: the first focusing lens, or the second focusing lens using at least one of: translation, or rotation.

10. The laser system of claim 7, wherein the laser delivery assembly further comprises at least one mirror optically coupled to at least one of: the first focusing lens, or the second focusing lens, wherein the positioning assembly is configured to rotate the at least one mirror.

11. The laser system of claim 1, wherein the laser source comprises a tunable pulsed laser source.

12. A method of modifying a substrate, the method comprising:
generating a laser beam comprising ultra-short pulses;
splitting the laser beam between a first beam delivery path and a second beam delivery path; and
focusing the laser beam from each of the first beam delivery path and the second beam delivery path to a focal point on a predefined plane within the substrate, the first beam delivery path intersecting the predefined plane at a first angle, and the second beam delivery path intersecting the predefined plane at a second angle, the focusing comprising adjusting the focus of the laser beam from the second beam path independently relative to the focus of the laser beam from the first beam delivery path;
wherein a first pulse from the first beam delivery path and a second pulse from the second beam delivery path are coincident at the focal point, and
wherein the laser beam from the second beam delivery path focuses light relative to the focus of the laser beam from the first beam delivery path independently to provide avoidance of laser energy excitation by the first pulse and the second pulse in at least one of: above the focal point, or above the predefined plane.

13. The method of claim 12, further comprising:
moving at least one of the focal point within the predefined plane and the predefined plane by moving at least one of: a first focusing lens, or a second focusing lens; and
wherein the moving at least one of the focal point within the predefined plane and the predefined plane comprises at least one of: translating, or rotating, at least one of: the first focusing lens, or the second focusing lens.

14. The method of claim 12, optically coupling at least one mirror to at least one of: the first focusing lens, or the second focusing lens; and
rotating, by the positioning assembly, the at least one mirror.

15. The method of claim 12, wherein the laser source comprises a tunable pulsed laser source, the method further comprising tuning the pulsed laser source.

16. The method of claim 12, wherein the second angle is different from the first angle.

17. The method of claim 12, wherein the second angle is equivalent to the first angle.

18. The method of claim 12, wherein the first beam delivery path and the second beam delivery path have different path lengths.

19. The method of claim 12, wherein the at least one focusing lens is at least one of: the first focusing lens, or the second focusing lens, is in a path of the laser beam before the beam splitter.

20. The method of claim 12, wherein the beam splitter is in a path of the laser beam before at least one of: the first focusing lens, or the second focusing lens as the at least one focusing lens.

* * * * *